United States Patent [19]

Benefice-Malouet et al.

[11] Patent Number: 4,983,776

[45] Date of Patent: Jan. 8, 1991

[54] PROCESS FOR THE PREPARATION OF FUNCTIONAL FLUORO DERIVATIVES

[75] Inventors: Sylvie Benefice-Malouet; Hubert Blancou, both of Montpellier; Auguste Commeyras, Clapiers, all of France

[73] Assignee: Societe Atochem, Puteaux, France

[21] Appl. No.: 343,743

[22] Filed: Apr. 27, 1989

[30] Foreign Application Priority Data

May 4, 1988 [FR] France ................... 88 06000

[51] Int. Cl.$^5$ ............ C07C 45/00; C07C 45/43
[52] U.S. Cl. ................... 568/490; 568/364; 568/437; 568/495
[58] Field of Search ............ 568/466, 488, 490, 495, 568/308, 316, 348, 437, 364, 449, 393

[56] References Cited

U.S. PATENT DOCUMENTS

| | | | |
|---|---|---|---|
| 2,568,500 | 9/1951 | Husted et al. | 568/495 |
| 2,574,832 | 11/1951 | Kharasch | 568/490 |
| 4,484,993 | 11/1984 | Ishikawa et al. | 568/490 |
| 4,760,195 | 7/1988 | Kubo et al. | 568/466 |
| 4,837,366 | 6/1989 | Murata et al. | 568/490 |

FOREIGN PATENT DOCUMENTS

| | | | |
|---|---|---|---|
| 0254652 | 1/1988 | European Pat. Off. | 568/407 |
| 2521987 | 8/1983 | France | 568/814 |

OTHER PUBLICATIONS

E. T. McBee, et al., Reactions of Perfluoronitriles With Grignard Reagents, pp. 917–919, Feb. 20, 1955.
Yu. V. Zeifman, et al., Combined Addition of Fluorocarbanions and Electrophilic Reagents to Fluoroolefins, pp. 212–215, Plenum Publishing Corporation (1983).
Yanchang Shen, et al., A Convenient Synthesis of Terminal Perfluoroacylacetylenes and Perfluoroalkynals, pp. 159–160, Communications (Feb. 1985).
Coe, et al., Aromatic Polyfluoro-Compounds, Part XI, Pentafluorophenyl-lithium and Derived Compounds, pp. 3227–3231, 622, J. Amer. Chem. Soc. (1962).
Vorozhtsov, Jr., et al., Preparation and Reactions of Pentafluorophenyl and Pentafluoronaphthylmagnesium Chlorides, Institute of Organic Chemistry, pp. 1135–1139, vol. 159, (1964).
Organometallic Compounds, p. 4046, vol. 62 (1965).

*Primary Examiner*—Werren B. Lone
*Attorney, Agent, or Firm*—Morgan & Finnegan

[57] ABSTRACT

The invention relates to the synthesis of functional fluoro derivatives and more particularly that of perfluorinated aldehydes of the type $R_F$-CHO where $R_F$ denotes a linear or branched perfluoroalkyl radical.

A perfluoroalkyl iodide $R_FI$ is reacted over the zinc-copper metal couple, in the presence of a radical initiator, with an amide $RCONR_1R_2$, R denoting a hydrogen atom or a methyl or ethyl radical, and each of $R_1$ and $R_2$ denoting a $C_1$–$C_4$ alkyl radical.

10 Claims, No Drawings

PROCESS FOR THE PREPARATION OF FUNCTIONAL FLUORO DERIVATIVES

FIELD OF THE INVENTION

The present invention relates to the field of functional fluoro derivatives and more particularly its subject-matter is the synthesis of perfluorinated aldehydes of the type $R_FCHO$ and of their hydrates $R_FCH(OH)_2$ where $R_F$ denotes a linear or branched perfluoroalkyl radical.

BACKGROUND OF THE INVENTION

These perfluorinated aldehydes are useful as starting materials for the synthesis of chemical products containing a perfluorinated chain and which can be used, for example, as a surface agent. In particular, they can be reduced to polyfluorinated alcohols $R_F$—$CH_2OH$.

Among the various currently known access routes to these perfluorinated aldehydes the following may be mentioned more particularly:

(1) The ozonolysis of compounds of the type $CF_3(CF_2)_nCH=CHR$, which makes it possible to obtain aldehydes of the type $CF_3(CF_2)_nCHO$ directly in a 25% yield. See German Patent No. 2,556,844 and British Patent No. 1,473,807.

(2) The reaction of perfluorobutyronitrile with a magnesium compound such as isopropylmagnesium bromide, leading to the formation of 37% of perfluorobutyraldehyde. See McBee et al., J. Am. Chem. Soc., 77, 917 (1955).

(3) The reaction of tetrafluoroethylene with $(CF_3)_3C$—$CH(NMe_2)_2$ leading, after hydrolysis, to the aldehyde $(CF_3)_3C$—$CF_2$—$CF_2$—$CHO$. See Zeifman et al., Dokl. Akad. Nauk., SSSR, 265, 2, 347 (1982).

It is also possible to report the preparation of acetylenic perfluorinated aldehydes $R_FC\equiv C$—$CHO$ in a yield of between 15 and 40% by a Wittig reaction between a perfluorinated acid chloride $R_FCOCl$ and a phosphorus ylide of the type $(C_6H_5)_3P=CH$—$CHO$, followed by a pyrolysis at 220° C. and 1333 Pa (Shen Yanchang et al., Synthesis, 2, 159 (1985)), as well as the preparation of perfluorobenzaldehyde in a yield of 40% by reaction of perfluoro-phenyl-lithium with N-methylformamide (Coe et al., J. Chem. Soc., 3227 (1962)) or in a yield of 62.4% by reaction of perfluorophenylmagnesium chloride with N-methylformanilide (Vorozhtsov et al., Dokl. Akad. Naut., SSSR, 159, 125 (1964) and CA, 62, 4045a (1965)).

It is further known, that perfluoroalkyl iodides $R_FI$ react with the zinc-copper metal couple and substrates such as $SO_2$ or $CO_2$, in dimethyl sulphoxide or dimethylformamide, to lead to zinc sulphonates and carboxylates, precursors of the corresponding perfluorinated acids. See French Patent Nos. 2,342,950; 2,373,503 and 2,374,287. It is also known that polyfluorinated iodides of the type $R_FCH_2CH_2I$ react with zinc-copper couple in dimethyl sulphoxide or dimethylformamide to produce the fluorinated alcohols $R_FCH_2CH_2OH$ after oxidation with gaseous oxygen and hydrolysis. See French Patent No. 2,521,987. These known reactions have been carried out in the absence of a radical initiator.

The above references are hereby incorporated by reference herein.

SUMMARY OF THE INVENTION

It has now been found that it is easily possible to gain access to perfluorinated aldehydes $R_FCHO$ and to their hydrates $R_FCH(OH)_2$, as well as to other functional fluoro derivatives (particularly ketones and amides) by reacting a perfluoroalkyl iodide $R_FI$ over the zinc-copper metal couple with an N,N-dialkylated amide used as solvent in the presence of a radical initiator.

DETAILED DESCRIPTION OF THE INVENTION

The process according to the invention applies more particularly to perfluoroalkyl iodides in which the linear or branched radical $R_F$ contains from 2 to 20 carbon atoms and, preferably, from 4 to 12 carbon atoms.

The zinc-copper metal couple to be used for implementing the process according to the invention may be obtained, for example, by adding zinc powder to a boiling solution of copper acetate in acetic acid, followed by washing the solid with acetic acid and drying. Copper salts other than the acetate can be used, for example the chloride or the sulphate in a hydrochloric acid-water medium. The Zn/Cu molar ratio may vary from 30 to 150, but it is preferably between 50 and 120. The quantity of zinc in the form of Zn/Cu couple to be used per mole of $R_FI$ may vary from 1 to 2 moles and is preferably between 1 and 1.5 moles.

Dimethylformamide is preferably used as the N,N-dialkylated amide which is used both as a reactant and as a solvent. But, it is generally possible to use the compounds $RCONR_1R_2$, R denoting a hydrogen atom or a methyl or ethyl radical, and each of $R_1$ and $R_2$ denoting a $C_1$-$C_4$ alkyl radical. The quantity of N,N-dialkylated amide to be used may vary from 1.5 to 5 moles per mole of $R_FI$ and is preferably between 1.8 and 2.2 moles.

The preferred radical initiator is azobisisobutyronitrile. But, it is generally possible to use any initiator, for example 4,4'-azobis(4-cyanovaleric) acid or ethyl chloroformate. The quantity of initiator to be used may vary from 0.01 to 0.1 mole per mole of $R_FI$ and is preferably between 0.02 and 0.04 mole.

The reaction takes place well at a temperature ranging from −20° C. to +25° C. It is preferably performed at approximately 0° C. by adding the perfluoroalkyl iodide rapidly to a dispersion of the Zn/Cu couple in the N,N-dialkylated amide containing the radical initiator. Because the reaction is exothermic, it is generally appropriate to cool the reaction mixture using any suitable means.

The functional fluoro derivative(s) formed may be isolated in a manner which is known per se, for example by filtration, phase separation, vacuum distillation or sublimation. When the N,N-dialkylated amide is of the formamide type, the distillation of the filtered reaction mixture generally yields a mixture of the perfluorinated aldehyde $R_FCHO$ and of the N,N-dialkylformamide. When this mixture is treated with water, the hydrate $R_FCH(OH)_2$ is formed and can be isolated by filtration and readily purified by sublimation. Its dehydration by distillation over $P_2O_5$ enables the aldehyde $R_FCHO$ to be obtained pure.

Although the process according to the invention is intended more particularly for the synthesis of perfluorinated aldehydes, if desired it can be directed towards the formation of other functional fluoro derivatives (ketones, amides) by means of the choice and/or the proportion of N,N-dialkylated amide.

EXAMPLE

The following examples illustrate the invention without limiting it.

EXAMPLE 1:

Synthesis of Perfluoroheptanal (a) Preparation of the Zn/Cu Metal Couple 6.5 g (0.1 mole) of zinc powder are added in small portions to a solution of 0.2 g (0.001 mole) of copper acetate in 10 ml of acetic acid, heated to boiling. After cooling, the product is washed several times with acetic acid and the metal couple is then recovered by decanting and the acetic acid is removed by evaporation under reduced pressure.

(b) Preparation of $C_6F_{13}CHO$

The freshly prepared Zn/Cu couple is then dispersed in 15 ml of dimethylformamide, to which 3 millimoles of azobisisobutyronitrile are then added. 44.6 g (0.1 mole) of perfluorohexyl iodide are then added quickly (approximately 8 minutes) with stirring, while the temperature of the reaction mixture is kept at approximately 0° C. by means of a cold alcohol or ice bath.

The organofluorinated portion is then removed by phase separation and is then filtered. By distillation of the filtrate under reduced pressure (133 Pa) 34 g of a mixture containing 70 mol% of perfluoroheptanal $C_6F_{13}CHO$ (i.e. 31.3 g) and 30 mol% of dimethylformamide (i.e. 2.7 g) are obtained, which corresponds to a 90% yield of perfluoroheptanal, based on the initial perfluorohexyl iodide. The molar percentages shown are determined by integrating the signals observed by $^1H$ NMR.

The same result is obtained if azobisisobutyronitrile is replaced with the same molar quantity of 4,4'-azobis (4-cyanovaleric) acid.

Perfluoroheptanal is obtained in its hydrated form $C_6F_{13}CH(OH)_2$, free from dimethylformamide, by sublimation.

EXAMPLE 2:

Synthesis of Perfluoropentanal

The procedure is as in Example 1, but with 34.6 g (0.1 mole) of perfluorobutyl iodide $C_4F_9I$. 26.5 g of a mixture containing 70 mol% of perfluoropentanal $C_4F_9CHO$ (i.e. 23.55 g) and 30 mol% of dimethylformamide (i.e. 2.95 g) are obtained, which corresponds to a 95% yield of perfluoropentanal, based on
the initial perfluorobutyl iodide.

EXAMPLE 3:

Synthesis of Perfluorononanal

When Example 1 is repeated with 54.6 g (0.1 mole) of perfluorooctyl iodide $C_8F_{17}I$, 40.7 g of a mixture containing 70 mol% of perfluorononanal $C_8F_{17}CHO$ (i.e. 38.05 g) and 30 mol% of dimethylformamide (i.e. 2.65 g) is obtained, which corresponds to an 85% yield of perfluorononanal, based on the initial perfluorooctyl iodide.

EXAMPLE 4

The procedure is as in Example 1, but with 30 ml of dimethylformamide. After reaction, the reaction mixture consists of two phases which are separated by decanting.

The lower phase is treated as in Example 1. 26.5 g of a mixture containing 70 mol% of perfluoroheptanal (i.e. 24.3 g) and 30 mol% of dimethylformamide (i.e. 2.2 g) are obtained, which corresponds to a 70% yield of perfluoroheptanal, based on the initial perfluorohexyl iodide.

The upper phase, distilled under reduced pressure and chromatographed, yields 7.8 g of the amide $C_6F_{13}CON(CH_3)_2$.

EXAMPLE 5

Example 4 is repeated, but with dimethylformamide replaced with 35 ml of dimethylacetamide. 16.3 g of methyl perfluorohexyl ketone $C_6F_{13}COCH_3$ and 17.6 g of the amide $C_6F_{13}CON(CH_3)_2$ are then obtained.

EXAMPLE 6

Example 4 is repeated but with dimethylformamide replaced with 40 ml of diethylformamide. The following are then obtained:

24.3 g of a mixture containing 80 mol% of perfluoroheptanal (i.e. 22.65 g) and 20 mol% of diethylformamide (i.e. 1.65 g), which corresponds to a 65% yield, based on the initial perfluorohexyl iodide;

10.9 g of the amide $C_6F_{13}CON(C_2H_5)_2$.

EXAMPLE 7

The procedure is as in Example 1-b, but performed at the ambient temperature (approximately 20° C.). After purification, 30.3 g of a mixture containing 70 mol% of perfluoroheptanal (i.e. 27.8 g) and 30 mol% of dimethylformamide (i.e. 2.5 g) are obtained, which corresponds to an 80% yield of perfluoroheptanal based on the perfluorohexyl iodide used.

EXAMPLE 8

The procedure is as in Example 1-b, but with azobisisobutyronitrile replaced with 1 g of ethyl chloroformate. 24.6 g of a mixture containing 70 mol% of perfluoroheptanal (i.e. 22.6 g) and 30 mol% of dimethylformamide (i.e. 2 g) are then obtained, which corresponds to a 65% yield.

Although the invention has been described in conjunction with specific embodiments, it is evident that many alternatives and variations will be apparent to those skilled in the art in light of the foregoing description. Accordingly, the invention is intended to embrace all of the alternatives and variations that fall within the spirit and scope of the appended claims.

We claim:

1. Process for the preparation of fluoro aldehydes, ketones or amides, comprising reacting a linear or branched $C_2$-$C_{20}$ perfluoroalkyl iodide $R_FI$ over a zinc-copper metal couple, in the presence of a radical initiator selected from azobisisobutyronitrile, 4,4'-azobis(4-cyanovaleric)acid and ethyl chloroformate, with an amide $RCONR_1R_2$, where R denotes a hydrogen atom or a methyl or ethyl radical, and each of $R_1$ and $R_2$ denotes a $C_1$-$C_4$ alkyl radical.

2. The process according to claim 1 for the preparation of perfluorinated aldehydes $R_FCHO$, wherein the amide $RCONR_1R_2$ is an N,N-dialkylformamide.

3. The process according to claim 2, wherein the amide is dimethylformamide.

4. The process according to claim 1, wherein the reaction is carried out at a temperature ranging from $-20°$ C. to $+25°$C.

5. The process according to claim 4, wherein the temperature is approximately 0° C.

6. The process according to claim 1, wherein $R_F$ contains from 4 to 12 carbon atoms.

7. The process according to claim 1, wherein from 1 to 2 moles of zinc in the form of a Zn/Cu couple, from 1.5 to 5 moles of amide $RCONR_1R_2$ and from 0.01 to 0.1 mol of radical initiator are used, per mole of perfluoroalkyl iodide.

8. The process according to claim 1, wherein the molar ratio Zn/Cu is between 30 and 150.

9. The process according to claim 8, wherein the molar ratio Zn/Cu is between 50 and 120.

10. Process for the preparation of fluoro aldehydes or ketones $R_FCOR$ or amides $R_FCONR_1R_2$ comprising reacting a linear or branches $C_2$–$C_{20}$ perfluoroalkyl iodide $R_FI$ over a zinc-copper metal couple, in the presence of a radical initiator selected from azobisisobutyronitrile, 4,4'-azobis(4-cyanovaleric)acid and ethyl chloroformate, with an amide $RCONR_1R_2$, where R denotes a hydrogen atom or a methyl or ethyl radical, and each of $R_1$ and $R_2$ denotes a $C_1$–$C_4$ alkyl radical.

* * * * *